United States Patent [19]
Levy

[11] Patent Number: 5,292,253
[45] Date of Patent: Mar. 8, 1994

[54] METHOD FOR REPAIRING TOOTH AND BONE TISSUE

[75] Inventor: Guy Levy, Tustin, Calif.

[73] Assignee: Laser Medical Technology, Inc., San Clemente, Calif.

[21] Appl. No.: 901,834

[22] Filed: Jun. 22, 1992

[51] Int. Cl.⁵ ............................................. A61C 5/00
[52] U.S. Cl. ................................... 433/215; 606/3
[58] Field of Search ............ 128/395; 433/215, 217.1, 433/29; 606/3, 40

[56] References Cited

U.S. PATENT DOCUMENTS

| | | | |
|---|---|---|---|
| 4,905,671 | 3/1990 | Serge et al. | 128/24 AA |
| 4,932,973 | 6/1990 | Gendler | 623/66 X |
| 4,961,707 | 10/1990 | Magnusson et al. | 433/215 |
| 5,032,445 | 7/1991 | Scantlebury et al. | 433/215 X |
| 5,090,908 | 2/1992 | Teumim-Stone | 433/215 |
| 5,171,148 | 12/1992 | Wasserman et al. | 433/215 |

FOREIGN PATENT DOCUMENTS

| | | | |
|---|---|---|---|
| 2597745 | 10/1987 | France | 433/215 |
| 1097293 | 6/1989 | U.S.S.R. | 433/215 |
| 1519681 | 11/1989 | U.S.S.R. | 433/215 |

OTHER PUBLICATIONS

"Proceedings of Laser in Orthopedic, Dental, and Veterinary Medicine" Progress in Biomedical Optics; 23-24 Jan. 1991, Los Angeles, Calif.; SPIE vol. 1424.

Primary Examiner—Gene Mancene
Assistant Examiner—Nicholas D. Lucchesi
Attorney, Agent, or Firm—Spensley Horn Jubas & Lubitz

[57] ABSTRACT

An opening in bone or tooth tissue is repaired by at least partially filling the opening with a calcium-containing material in a moldable state and a protein gel; and applying to the gel laser radiation in a manner to weld that material to one of the bone or tooth tissue adjacent the opening and the calcium-containing material without causing harmful side effects to the bone or tooth tissue.

10 Claims, 1 Drawing Sheet

METHOD FOR REPAIRING TOOTH AND BONE TISSUE

BACKGROUND OF THE INVENTION

The object of the present invention is the use of a laser to weld fibrin or collagen to repair periodontal disease and enhance bone reconstitution in the healing of periodontal pockets. The technique can also be used for the repair of cracked teeth.

It has been demonstrated that the use of collagen helps in the repair of periodontal problems. According to one example, implants of collagen are positioned on calcium phosphate packed where bone is missing after recession due to a disease. In a procedure according to this example, periodontal surgery is usually performed to clean the recessed area by removing granulation tissue and cleaning the cementum of the adjacent teeth. Then, the missing bone is filled with a mass of calcium phosphate or hydroxyapatite constituting a graft. Then the collagen implant is positioned at the location of the bone recession and the flap of gingiva is sutured to close the diseased area. The collagen prevents the epithelium from invading the graft. This procedure has been found to promote acceleration of the healing process and reconstruction of bone by replacing or penetrating the graft.

In the field of dentistry, lasers have been used to cut diseased soft tissue. In the field of orthopedics, lasers have been used under experimental conditions to weld a fibrin clot on a meniscus in a joint. Fibrin clot is known in orthopedics to be used to repair cartilage without laser welding or to suture peripheral nerves. References include Forman et al, "Laser Effects on Fibrin Clot . . . ", SPIE Vol. 1424, Lasers in Orthopedics, Dental and Veterinary Medicine 2 (1991).

The laser used in previous studies was a semiconductor gallium aluminum arsenide laser.

SUMMARY OF THE INVENTION

It is a primary object of the present invention to provide better repair of recesses or cracks in tooth or bone tissue, using calcium-containing materials and protein gels. A specific object of the invention is to aid healing of a treated region subsequent to such treatment.

The above and other objects are achieved, according to the present invention, by a method for repairing an opening in bone or tooth tissue, which method includes at least partially filling the opening with a calcium-containing material in a moldable state and a protein gel, and applying to the gel laser radiation in a manner to weld the calcium-containing material to the bone or tooth tissue adjacent the opening and the calcium-containing material without causing harmful side effects to the bone or tooth tissue.

DESCRIPTION OF THE PREFERRED EMBODIMENTS

Figure 1:
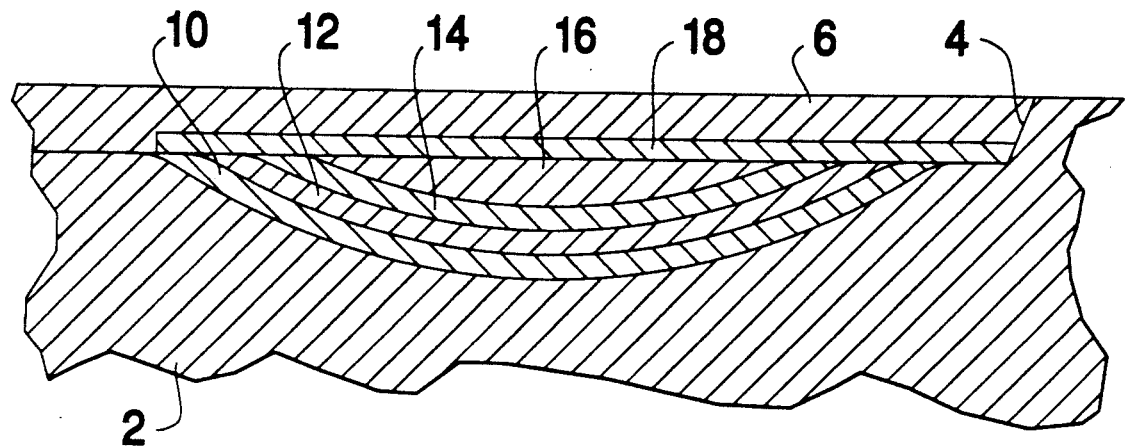
FIGS. 1 and 2 are cross-sectional detail views illustrating two embodiments of the method according to the invention.

The invention relates to the use of lasers to weld a protein gel, such as collagen, fibrin or gelatin, plasmin and/or plasma in periodontal pockets on or mixed with grafted material which is positioned on the remaining bone structure. This gel may be stained a dark color to enhance absorption of laser radiation energy, to thereby permit the level of energy delivered by the laser radiation to be reduced. The same operation can be carried out at higher laser radiation energy levels, without dye. If gelatin is used, it may, for example, be Type B, made from bovine skin.

The gel can be mixed with hydroxyapatite or monobasic, dibasic or tribasic calcium phosphate and then exposed to the laser radiation.

Different lasers can be used for this operation, depending on the type of dye used and the absorption of the laser radiation by hydroxyapatite, by calcium phosphate, or by mixtures thereof, possibly mixed with a gel.

Black dyes have been demonstrated to absorb radiation produced by the Nd:YAG laser, at 1.06 microns wavelength, as well as radiation at wavelengths between 400 and 750 nanometers. Red dyes such as sudan red absorb radiation at the wavelength produced by the Argon laser as well as the double frequency Nd:YAG wavelength, and the wavelength produced by the Ruby laser.

Holmium and Erbium YAG lasers can be used also without dye since their wavelengths are absorbed by hydroxyapatite and they are able to give the thermal effect necessary to weld gels such as collagen and fibrin. $CO_2$ lasers also have a similar effect and are not sensitive to dyes.

Semiconductor lasers, such as gallium arsenide lasers, produce radiation which is absorbed by many dyes. The primary output of this laser is at a wavelength of 808 nanometers. In this particular application, black dyes and red dyes give more interesting results for welding with semiconductor lasers. Excimer lasers operating in the UV wavelength region can be used without dyes for the same application.

Generally, the Nd:YAG can be used in the continuous wave mode or in the pulsed mode. The average power output of these lasers is between 5 watts and 10 watts. However, since the beam must be defocussed on large areas of the order of 1 to 5 cm$^2$, lasers having a higher average power output can be used. The pulse duration can be in the range of microseconds to 100 milliseconds, but shorter pulse durations in the nanosecond range can also be used for treating small areas and spots.

The repetition rate can be in the range of 10 to 100 hertz for longer pulses or 10 to 1000 hertz for shorter pulses.

Excimer lasers producing outputs at 190 nanometers to 308 nanometers can be used only in the pulse mode and the treatment is carried out to create a total energy density, or fluence, at the treatment surface in the range of 1-12 joules/cm$^2$ for the complete procedure according to the diameter of the irradiated spot. The radiation pulse duration call be in the range of nanoseconds to 100 msec, repetition rate can be the same as described above for an Nd:YAG laser.

Holmium and Erbium YAGs can also be used in the pulsed mode and a fluence of 5 joules/cm$^2$ is required at a minimum for the Erbium or Holmium YAG. A fluence of 1-20 joules/cm$^2$ can be used for the Excimer lasers. For these lasers, the pulse duration should be 1 $\mu$sec to 1 msec; the repetition rate from 1 to 50 Hz.

Other lasers can be used simultaneously with a YAG laser, e.g. with a Nd:YAG, Erbium YAG, or Holmium YAG. By way of example, an argon laser could be used simultaneously with a YAG laser. In this case the average power for the argon laser can be under 1 watt and the visible emission of the argon laser can be used to aim the beam of the YAG laser.

Sudan red can preferably be used as a dye added to the mixture of protein gel and calcium-containing material. The advantage of such a combination of lasers is the possible use of the Nd:YAG for example for bone resection or tooth amputation and the argon laser for the specific use described here. In this case, the exposure time on the irradiated area is relatively long, 2 to 5 minutes, and the spot size is small, in the range of a square millimeter. To shorten treatment time, for a specific application, more powerful argon lasers, with a minimum average power of 5 to 10 watts must be used with a short average exposure time. The fluence can be between 10 and 100 joules/cm$^2$ over a period of 10 to 20 seconds. When these values are used, dye is not required.

According to the invention, all argon laser can be used alone to weld or fuse a protein gel. This allows procedures according to the invention to be carried out with less expensive apparatus.

The material employed to cover a graft or fill a gap can be protein gel alone or in mixture with a calcium-containing substance. The protein gel is preferably composed of fibrin and/or collagen, and the calcium-containing substance is preferably composed of a calcium phosphate and/or hydroxyapatite. The use of a mixture with calcium phosphate is recommended in the field of orthopedics most specifically for bone repair. The advantage of this technique over the state of the art is that the addition of calcium phosphate significantly aids the repair of cracks and fractures in bone.

In dentistry, these mixtures can be used to repair fractured teeth or cracked teeth or bone. They can even be used to repair fractured teeth or cracked teeth in regions not covered by gum. For this purpose, laser radiation can be applied and dye can be employed in accordance with the preceding description.

The proportion of hydroxyapatite or calcium phosphate in the mixture with protein gel can be between 5 and 40%, with a higher rate of success having been achieved with a proportion between 10 and 20%.

The procedure for repairing a pocket, or recess, in bone in the jaw can be as follows. After opening a flap in the gum on the area to be lased, this area is cleaned, which operation can also be performed with a laser beam ($CO_2$, YAG, or Excimer). Calcium phosphate is packed gently in layers, each layer having a thickness of 1 to 3 millimeters, on the bone structure, or oil the bone and tooth structure, to form a graft. Then, this calcium phosphate may be lased or not, depending on the technique chosen by the dentist. Then, premixed protein gel, possibly mixed with additional calcium phosphate, and also possibly stained with a specific dye, selected according to the laser being used, is applied to cover the graft, i.e. the mass of previously applied calcium phosphate. If sudan red is used, it can be in a concentration of 2%, and it will stay in the mixture in a manner appropriate for absorbing energy delivered by an argon laser.

The premix is welded on the hard tissue, i.e. the tooth or bone, depending on the surface to be welded and irradiated. The fluence is chosen for example at 20 joules/cm$^2$ for the complete treatment with an exposure of 10 seconds for an argon laser, for example at a high power of the order of 40 watts.

After a first layer of tile premix has been formed and irradiated, a second layer call be added, followed by a third layer, etc.

Then the flap is sutured or is welded with protein gel.

FIG. 1 shows an example of the method according to the invention for repairing a recess formed in a bone region 2 in the mouth. Access to the region is initially attained by forming an incision 4 in gum layer 6 in a manner to form a flap of gum which can be lifted to expose the region.

Then, the recess in bone region 2, which may have been created by periodontal disease, is cleaned out.

After the recess has been thus prepared, a first layer 10 of a mixture of protein gel and calcium-containing material is packed to a thickness of 1-3 mm onto the bottom of the recess and laser radiation is applied to melt the protein gel with the result that the calcium-containing material in layer 10 is welded to bone adjacent the bottom of the recess.

In a second filling step, a second layer 12 of a mixture of protein gel and calcium-containing material is packed onto layer 10. Layer 12 may also have a thickness of 1-3 mm. Laser radiation is applied to melt the gel in layer 12 so that the calcium-containing material in layer 12 is welded to layer 10.

This procedure is repeated with respect to layers 14 and 16 until the recess is completely filled.

Then the flap of gum layer 6 may be returned to its original position and sutured, or a layer 18 of protein gel may be applied, the gum layer flap returned to position and laser radiation applied to weld layer 18 to gum 6 and bone.

Figure 2:
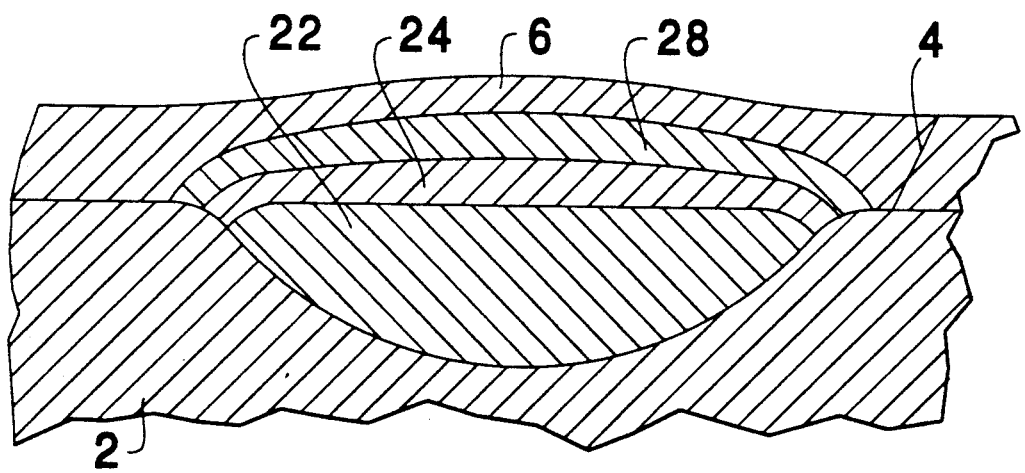

A second embodiment of the method according to the invention is shown in FIG. 2. Here, a mass 22 composed only of calcium-containing material is packed into the recess in bone region 2. Then, a layer 24 of protein gel is applied and melted by laser radiation to be fused to mass 22 and portions of region 2 so as to form a cover which immobilizes mass 22.

Finally, incision 4 may be closed either by suturing or by welding, with the aid of a protein gel layer 28, as described with reference to FIG. 1.

During the subsequent healing process, bone tissue may replace the calcium-containing material or grow into interstices thereof.

To implement the invention, the gel may be, prior to lasing, in the form of a liquid, possibly a viscous liquid.

While the description above refers to particular embodiments of the present invention, it will be understood that many modifications may be made without departing from tile spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A method for repairing an opening in bone or tooth tissue comprising: at least partially filling the opening with a calcium-containing material in a moldable state and a protein gel; and applying to the gel laser radiation in a manner to weld the gel to one of the bone or tooth tissue adjacent the opening and the calcium-containing material without causing harmful side effects to the bone or tooth tissue.

2. A method as defined in claim 1 wherein said step of filling comprises: forming a mixture of the gel and the calcium-containing material; and depositing successive layers of the mixture to at least partially fill the opening.

3. A method as defined in claim 2 wherein said step of applying laser radiation is performed to apply laser radiation after deposition of each layer.

4. A method as defined in claim 3 wherein the bone or tooth tissue is normally covered by a layer of soft tissue, and further comprising, after completion of said steps of filling and applying, depositing a layer of protein gel on the last layer of the mixture, covering the protein gel layer with the soft tissue, and applying laser radiation to weld the protein gel layer to the soft tissue.

5. A method as defined in claim 4 wherein the calcium-containing material is at least one of hydroxyapatite and a calcium phosphate, and the protein gel is at least one of fibrin, collagen, gelatin, plasmin and plasma.

6. A method as defined in claim 1 wherein said step of filling comprises: placing a mass of the calcium-containing material in the opening; and covering the mass of material with a layer of the protein gel.

7. A method as defined in claim 6 wherein the bone or tooth tissue is normally covered by a layer of soft tissue, and further comprising, after completion of said steps of filling and applying, depositing a layer of protein gel on the last layer of the mixture, covering the protein gel layer with the soft tissue, and applying laser radiation to weld the protein gel layer to the soft tissue.

8. A method as defined in claim 7 wherein the calcium-containing material is at least one of hydroxyapatite and a calcium phosphate, and the protein gel is at least one of fibrin, collagen, gelatin, plasmin and plasma.

9. A method as defined in claim 1 wherein the opening being repaired is one which was created in bone by periodontal disease.

10. A method as defined in claim 1 wherein the opening is constituted by a crack in a tooth.

* * * * *